(12) United States Patent
Valsesia et al.

(10) Patent No.: US 9,395,363 B2
(45) Date of Patent: Jul. 19, 2016

(54) SPR SENSOR DEVICE WITH NANOSTRUCTURE

(75) Inventors: Andrea Valsesia, Ranco (IT); Franco Marabelli, Pavia (IT); Silvia Giudicatti, Tirano (IT); Gerardo Marchesini, Laveno (IT); François Rossi, Cittiglio (IT); Pascal Colpo, Angera (IT)

(73) Assignees: THE EUROPEAN UNION, REPRESENTED BY THE EUROPEAN COMMISSION, Brussels (BE); PLASMORE SRL, Ranco (Varese) (IT)

( * ) Notice: Subject to any disclaimer, the term of this patent is extended or adjusted under 35 U.S.C. 154(b) by 0 days.

(21) Appl. No.: 14/232,359

(22) PCT Filed: May 31, 2012

(86) PCT No.: PCT/EP2012/060310
§ 371 (c)(1),
(2), (4) Date: Jan. 13, 2014

(87) PCT Pub. No.: WO2013/007448
PCT Pub. Date: Jan. 17, 2013

(65) Prior Publication Data
US 2014/0134714 A1  May 15, 2014

(30) Foreign Application Priority Data
Jul. 14, 2011  (EP) ..................................... 11174058

(51) Int. Cl.
*G01N 33/543* (2006.01)
*G01N 21/552* (2014.01)

(52) U.S. Cl.
CPC ........ *G01N 33/54373* (2013.01); *G01N 21/554* (2013.01)

(58) Field of Classification Search
CPC ....................... G01N 33/54373; G01N 21/554
See application file for complete search history.

(56) References Cited

U.S. PATENT DOCUMENTS

| | | | |
|---|---|---|---|
| 2006/0192115 A1* | 8/2006 | Thomas | G01N 21/6458 250/306 |
| 2008/0316490 A1 | 12/2008 | Yen et al. | |
| 2009/0021727 A1 | 1/2009 | Sepulveda Martinez et al. | |

FOREIGN PATENT DOCUMENTS

| | | |
|---|---|---|
| EP | 2264438 A1 | 12/2010 |
| WO | 2008039212 A2 | 4/2008 |
| WO | 2010130045 A1 | 11/2010 |

OTHER PUBLICATIONS

International Preliminary Report of Patentability for corresponding application PCTEP2012/060310 filed May 31, 2012, Mail date Oct. 11, 2013.

(Continued)

*Primary Examiner* — Lore Jarrett
(74) *Attorney, Agent, or Firm* — Cantor Colburn LLP

(57) ABSTRACT

A sensor device comprises a dielectric substrate (52); and a metal layer (53) on the substrate (52) with at least one array of cavities (54) therein and adapted to support L-SPR, each of the cavities (54) in the metal layer (53) having an opening (56) and a closed bottom (58) and widening from opening to bottom. A bed of dielectric material (62) is provided over the bottom (58) of each cavity (54) to reduce its apparent depth, the bed surface (62) being functionalized to bind to receptor moieties (64). This sensor device is particularly designed for SPR detection, but can be used in other detection techniques.

22 Claims, 3 Drawing Sheets

(56) References Cited

OTHER PUBLICATIONS

International Search Report or corresponding application PCTEP2012/060310 filed May 31, 2012, Mail date Jul. 5, 2012.
Li, J. et al, "Studies of the plasmonic properties of two-dimensional metallic nanobottle arrays", Applied Physics Letters 92, 213106, 2008.
Parsons, J. et al."Localized surface-plasmon resonances in periodic non-diffracting metallic nanoparticle and nanohole arrays" Physical Review B 79, pp. 073412-1-073412-4, (2009).
Giudicatti S. et al.: "Plasmonic resonances in nanostructured gold/polymer surfaces by colloidal lithogragphy", Physical Status Solidi A 207, No. , 935-942 (2010), XP002665166.
Valsesia A, "Fabrication of nanostructured surfaces for the development of advanced biointerfaces", Scientifica Acta 1, No. 1, pp. 153-157 (2007), XP002665167.
Mannelli I et al.: "Bioadhesive nanoareas in antifouling matrix for highly efficient affinity sensors", Proceedings of the SPIE—The International Society for Optical Engineering USA, vol. 7035, 2008, pp. 70350Y-10-70350Y-10, XP002665168.

F. Eftekhari; et al., Development of Portable SPR Sensor Devices Based on Integrated Periodic Arrays of Nanoholes, Proc. SPIE 7356, Optical Sensors 2009, 73560C_1 to 73560C_3, Dec. 31, 2009.
H.M. Chen, et al., Three-dimensional composite metallodielectric nanostructure, Department of Electrical of Computer Engineering, Applied Physics Letters, (2009), pp. 073117-1-3, vol. 94, Issue 7, University of California, San Diego, California.
J.S. Bouillard, et al. Optical transmission of periodic annular apertures in metal film on high-refractive index substrate, Applied Physics Letters, May 2010; 96(20):201101-201101-3. DOI: 10.1063/1.3427390.
K.J. Klein Koerkamp, et al., Strong Influence of Hole Shape on Extraordinary Transmission through Periodic Arrays of Subwavelength Holes, The American Physical Society, (2004), pp. 183901-1-3, vol. 92, No. 18.
R.L. Eriksen, et al., Fabrication of Large Area Homogeneous Metallic Nanostructures for Optical Sensing Using Colloidal Lithography, Microelectric Engineering (2010) pp. 1471-1474.

* cited by examiner

SPR SENSOR DEVICE WITH NANOSTRUCTURE

FIELD OF THE INVENTION

The present invention generally relates to surface plasmon resonance based sensing systems and more specifically to a SPR sensor device with a nanostructure suitable for use i.a. in chemical, biochemical, biological, biomedical, pharmaceutical and physical testing.

BACKGROUND OF THE INVENTION

There are many known sensors using the excitation of surface plasmons, termed Surface Plasmon Resonance (SPR) Sensors, for detecting refractive index changes in a sample adjacent to the sensor surface. Such SPR sensors are used e.g. for quantifying concentrations of substances in chemical, biochemical, biological, biomedical or pharmaceutical research, in clinical or food diagnosis or in environmental measurements (e.g. detection of gas or wastewater), etc. Many SPR sensors can perform fast, parallel and massive inspections, which make these sensors also convenient for quantifying molecular interactions, in particular for studying the affinity and the real-time reaction kinetics between two or more interacting molecules.

SPR sensors rely on the well-known SPR phenomenon, which involves one or more surface-bond electromagnetic waves that propagate at an interface between a metallic material (typically gold or silver) and a dielectric material. Each surface-bond electromagnetic wave, which is due to a collective oscillation of free electrons at the metal-dielectric interface, propagates with its highest intensity parallel to this interface and decays exponentially away from this interface.

The most commonly used techniques for excitation of SPR exploit a prism in the Kretschmann configuration. In such case, the prism is covered with a noble metal layer supporting surface plasmons, and SPR is optically excited through the prism. Indeed, light can excite the resonance of surface plasmons at a metal-dielectric interface if an interface-parallel component of the incident light and a surface-bond electromagnetic wave of the SPR both have matching frequencies and matching wavelengths. In the resonance condition, the incident light is absorbed by the metal-dielectric interface so as to couple with the surface-bond electromagnetic wave. It is then possible to observe this absorption by detecting for example a reduction in the intensity of the light that is transmitted or reflected by the metal-dielectric interface. The coupling condition between light and surface plasmon waves being very sensitive to refractive index changes of the dielectric medium close to the metal-dielectric interface, SPR sensors take advantage of this sensitivity in the resonance coupling condition for detecting changes in the refractive index of a dielectric medium by measuring the decrease in intensity of light reflected from the metal-dielectric interface, while the latter is illuminated with an SPR exciting light beam.

SPR finds particular application in biosensor systems capable of detecting interactions between biomolecules or biochemical molecules, for example interactions between antigens and antibodies, enzymes and ground substances, endocrines and receptors, nucleic acids and nucleic acids, etc. In particular, many SPR biosensor systems have bio-receptors attached on their sensor surface so as to detect changes in the light-SPR coupling condition caused by refractive index changes at the sensor surface when biochemical molecules or biomolecules interact with (bind to) these bio-receptors. Such biosensor systems are suitable for measuring for example concentrations of biomolecules or biochemical molecules in solutions, etc.

Currently, there are a variety of laboratory equipment based on SPR sensing. US patent application No. 2009/021, 727 describes bio-sensors based on the Kretschman configuration.

Another SPR biosensor system for detecting biochemical molecules is known from US°2008/316,490 and employs a metal grating instead of a prism.

More recently, the discovery of localized surface plasmon resonance (L-SPR) phenomena and enhanced transmission through metallic subwavelength periodic structures, have shown great promise to significantly increase the size of the detection array, supporting high throughput applications. For L-SPR applications, the simplest and most versatile technology that has been explored in a broad range of technological areas is the so-called nanohole array sensing configuration. In its classical approach, the SPR sensor comprises a dielectric substrate covered with a layer of noble metal in which a periodic array of nanoholes is formed, i.e. holes having subwavelength dimensions.

Such L-SPR based sensors with nanohole arrays are e.g. described in WO2008/039212, WO2010/130045 and by Parsons, J. et al. in "Localized surface-plasmon resonances in periodic non-diffracting metallic nanoparticle and nanohole arrays" (PHYSICAL REVIEW B 79, 073412 (2009)).

Giudicatti, S. et al. in "Plasmonic resonances in nanostructured gold/polymer surfaces by colloidal lithography", PHYSICA STATUS SOLIDI (A), vol. 297, April 2010 (April 2010), pages 935-942 describe a colloidal lithography procedure to prepare a LSPR supporting structure consisting of a gold film perforated by polymeric pillars arranged in a 2D hexagonal array.

The use of colloidal lithography in the preparation of SPR sensors is also disclosed in EP 2 264 438; and in "Bioadhesive nanoareas in antifouling matrix for highly efficient affinity sensors" by Mannelli et al., PROCEEDINGS OF THE SPIE—USA vol. 7035, 2008, pages 70350Y-1-70350Y-10.

BRIEF SUMMARY OF THE INVENTION

The invention provides a sensor device of the nanohole array type for SPR sensing that has an enhanced sensitivity.

While working on the instant invention, the present inventors have observed that whereas current technologies have allowed tuning the geometry of nanoholes to tailor their electromagnetic response, the resulting geometry may however not be optimal having regard to the biological detection process. In particular the present inventors have observed that the position of the biomolecular receptors affixed on the metal and in the holes are often improperly located to ensure the most efficient detection.

This problem in mind the present inventors have devised a plasmonic sensor device having a structure that permits ensuring that the binding of a ligand/analyte to a receptor occurs within a region having a strong electrical field density.

Accordingly, a sensor device, in particular a SPR sensor device, in accordance with the present invention comprises a dielectric substrate and a metal layer on said substrate adapted to support L-SPR. The metal layer has at least one array of cavities therein, each of said cavities having a depth, an opening and a closed bottom, and said cavities widening from opening to bottom.

It shall be appreciated that a bed of dielectric material is provided over the bottom of each cavity so that the cavity offers a reduced depth (the apparent depth) from its opening, the bed surface being functionalized to have binding affinity to receptor moieties.

A first aspect to be noticed is the widening shape of the cavity that permits strengthening the electric field about the opening of the cavity. Secondly, in order to bring the receptors closer to this region, so that the binding occurs in this strong density region, the bottom of the cavity is filled by dielectric material that forms a bed, which reduces the apparent depth of the cavity. Hence, the apparent depth corresponds to the residual depth available between the top/opening of the cavity and the surface of the bed.

In addition, the functionalized surface of the bed allows attaching thereon receptor moieties that will, during the assays and tests, bind with corresponding analytes/ligands that may be present in the sample under test.

In doing so, the receptor moiety is close to the strong electric field and the analyte binding thereto will actually be in this strong electric field region.

The present design thus allows designing the cavities in such a way as to meet desired electromagnetic specifics, while at the same time optimizing the position of the receptor moieties and of the complex that is formed in use, for optimal detection.

As used herein, the terms "receptor moiety" designates any kind of substance to be attached to the sensor as probe substance and having a defined binding specificity to an analyte to be detected. The receptor moiety may be any molecule, chemical, natural or biological substance or part thereof; for bioassays the receptor moieties may namely comprise: antigens/antibiodies, enzymes, proteins, oligonucleotides etc. The term "analyte" in turn designates any molecule, chemical substance, biomolecule or constituent of interest that is to be detected by means of the present sensor as a result of the binding specificity of the analyte with the receptor moiety attached on the sensor device. The analyte may be any type of ligand, molecule, biological substance, e.g. proteins, enzymes, peptides, organic and inorganic chemical substances, oligonucleotides, antibodies, etc. in general any kind of molecule that can be recognized by a specific biochemical reaction.

As for the shape of the nanocavities, continuous or stepped frusto-conical or trapezoidal shapes are preferred. However, those skilled in the art may devise any appropriate shapes, widening from top to bottom, that results in a strong electrical field pattern around the cavity opening.

As it will be understood, the apparent depth of the cavities is adapted in function of the type, and in particular depending on the length, of the receptor moiety and the analyte. The thickness of the dielectric bed in the cavity is thus advantageously designed such that upon binding of the analyte to the receptor moiety, the analyte is at least partially located in the region of strongest electric field. This implies that the binding extremity of the receptor moiety is contiguous to, or partially penetrates in, the region of strongest electric field. In this connection it may be noticed that the bed thus generally has a thickness (or height, i.e. the distance from the cavity bottom to the top surface of the bed) that is inferior to the cavity depth (or height).

For biological applications, the bed thickness is preferably such that the apparent depth lies in the range of 10 to 30 nm from the opening, more preferably between 15 and 25 nm.

The bed may be made from any appropriate dielectric material that can be functionalized with or for a receptor moiety adapted to detect an analyte of interest. The bed may for example comprise ppAA or nylon.

It is further to be noted that the bed may be made from one single material, or comprise two or more layers of dielectric material, where the thickness of each layer contributes to the global thickness of the bed and thus permits to adjust the apparent depth of the cavity. In such case it is the topmost layer that should have the functionalization ability. For example, a first layer of dielectric material such as ppAA or nylon with a thickness t1 may be formed; and a subsequent layer, having a thickness t2, of any suitable functionalized dielectric, e.g. porous dielectric including hydrogels, can be formed on the first layer. The global thickness T of the bed is than $T=t1+t2$; and where the depth of the cavity in the metal layer is $d_C$, the apparent depth $d_A$ is calculated as $d_A=d_C-T$.

In this connection one may further note that the functionalized layer may include molecules/moieties forming the receptor moieties, so that it is not required to locate receptor moieties on the substrate before use thereof.

In one embodiment, the metal layer has a thickness of at least 100 nm, preferably at least 120 nm. In practice, the metal layer may have a thickness in the range of 100 to 200 nm.

The cavities dimensions are in the nanometer range and, as it is known, in order to stimulate surface plasmons, the cavities have sub-wavelength dimensions, i.e. below the wavelength of the incident light.

The cavities in the metal layer are typically through bores, whereby a cavity's closed bottom is formed by the substrate surface. The cavities in the metal layer preferably have a depth of at least 100 nm, and more preferably in the range of 100 to 200 nm.

Furthermore, for operation in general with probe light selected from the UV-VIS-NIR spectrum, the cavities may be designed to have an opening width (say diameter or equivalent diameter) in the range of 50-250 nm, while the bottom width may be in the range of 100-450 nm.

In this context as well, the periodicity of the nanocavity array, i.e. the distance between the center of two cavities, may be in the range of 200 to 1000 nm.

Any metal adapted for L-SPR may be used for the L-SPR supporting metal layer. The metal may namely be selected from the group comprising: gold, silver, copper, platinum, aluminium or an alloy comprising one or more thereof.

Advantageously, the metal layer is covered by a thin anti-fouling layer that tends to prevent adhesion of proteins. As a result, the attachment of the receptor moieties at the surface of the dielectric bed, with its functionalized surface, is more easily carried out. And during testing, less proteins and analytes will tend to adhere to the metal, which will improve the signal to noise ratio.

In the context of the present application, the term "dielectric", as used for the substrate and the bed material, is meant to encompass materials that are not "conductors" and able to be polarized by the plasmon field and accordingly, and hence comprises dielectric materials such as sapphire, glass or polymers, but also appropriate semiconductor materials.

For ease of use, a microfluidic layer may be provided on top of the metal layer, as is usual in the art. Such microfluidic layer typically comprises channels arranged to selectively bring test samples in contact with a respective array of cavities.

Typically, one array of cavities will be associated with one type of receptors. Hence, the metal layer may comprise a plurality of cavities arrays, where each of the array then comprises a respective type of receptor moiety.

The present sensor may be used in a SPR analysis system with conventional illumination and light analysis system, whether with photodetectors configuration or with an imaging system.

In this connection, it may be noticed that for use in SPR imaging/microscopy the present SPR will have substantially enhanced performance over conventional SPR and L-SPR sensors. It is known that with conventional sensors, the probe light is selected as a trade-off between sensitivity and lateral resolution. By contrast, it will be appreciated that in the present SPR sensor, which uses nano-cavities arrays, the plasmons are confined in a narrow area, which leads to a fine lateral resolution (typically between 100 and 500 nm). In addition, the present cavity structure with the bed reducing the cavity depth allows positioning the target moieties in the strong electrical field for maximum sensitivity. As a result, SPR imaging can be performed at both high lateral resolution and high sensitivity.

The present sensor device can be used in a great deal of SPR analyses, depending on the type of receptor moieties attached at the bed surface. Amongst others, the present SPR sensor device may find application for testing in the chemical, biochemical, biological, biomedical, pharmaceutical and physical fields. More particularly, the present SPR sensors may used e.g. for quantifying concentrations of substances in chemical, biochemical, biological, biomedical or pharmaceutical research, in clinical or food diagnosis or in environmental measurements (e.g. detection of gas or wastewater), etc.

It will be further appreciated that the structure of the present sensor device can be of interest in molecular, chemical and/or biochemical detection techniques other than surface plasmon-based detection systems. In particular, the present sensor can be advantageously used in detection/analysis techniques where the localization and the enhancement of the electromagnetic field, as allowed by the present invention, is reflected in an enhancement of the detection signal, which can be optical, thermal, electrical, etc. Examples of such techniques are:

a. Surface Enhanced Raman Spectroscopy (SERS). In standard Raman Spectroscopy the monochromatic light from a laser excites the vibrational modes of molecules. These modes can be observed in the spectrum of the reflected light as positive peaks. The spectral position of the peaks (the Raman Spectrum) is characteristic of the molecule (as a fingerprint). Raman Spectroscopy is a unique way to determine directly the presence and the amount of different molecules present in a compound. In conventional SERS a nanostructured sensor surface enhances the Raman signal (which is normally very weak) making possible to determination of substances at lower concentration. The sensor device according to the present invention can advantageously be used in SERS. In such case the SERS enhancement occurs (as in the Surface Plasmon Resonance technique) at the top of the cavity and can be located by tuning the size and the shape of the cavities. Exactly as in the case of L-SPR analysis, with the present sensor device it is possible to locate the molecules to be detected exactly where the SERS enhancement is maximum and thereby improve signal sensitivity.

b. Fluoresce Spectroscopy. In standard fluorescence spectroscopy a fluorescent molecule (fluorophore) is excited by a laser light and emits fluorescent light at a different wavelength. This technique is used as a quantitative analytical method for determining the concentration of molecules, proteins, DNA, etc. With the present invention, when the fluorophore (conjugated with the secondary antibody or the DNA sequence making the recognition) is located in the region where the electric field is maximum, the sensitivity (i.e. the intensity of the fluorescent light) can be significantly enhanced.

c. In Matrix Assisted Laser Desorption Ionization (MALDI) and in Surface Assisted Laser Desorption Ionization (SALDI) a high-density laser beam is used to induce the desorption of the analytes from the surface in order to create ions that can be analyzed by a Mass Spectrometer. This is a very sensitive and very precise analytical technique for directly determining the concentration of any molecule. When employing the present sensor device in SALDI, the molecules to be analyzed will be located where the intensity of the Laser light (inducing the desorption) is maximum, hence increasing the efficiency of the analysis.

It may be noticed that in these different analysis techniques, surface plasmons are also locally stimulated by the incident light and thus the enhanced electrical field is obtained at the opening of the cavities, thanks to the particular shape of the cavities, as in SPR "only" analysis.

BRIEF DESCRIPTION OF THE DRAWINGS

The present invention will now be described, by way of example, with reference to the accompanying drawings, in which.

DETAILED DESCRIPTION a) Conventional L-SPR Sensor Design

As it is known to those skilled in the art, sensors based on SPR effect rely on two types of plasmonic resonant effect:
1) Sensors based on Surface Plasmon Polaritons (SPP) which are traveling waves at the interface between a dielectric and noble metal;
2) Sensors based on Localized Surface Plasmon Resonances (L-SPR), which are standing waves localized inside dielectric nanocavities in a noble metal material or, equivalently standing waves localized inside noble metal nanostructures in or on a dielectric medium.

Of course, in both cases the sensors are able to detect variations of the refractive index at the metal interface.

It is to be noted that in SPR biosensors the microscopic (or local) sensitivity determines the overall sensitivity of the sensor. The local sensitivity is related to the extension length of the electric field of the plasmonic resonance in the dielectric surrounding the metal. This length is called penetration depth.

Typically, the penetration depth of L-SPR is of the order of magnitude of 10 nm. Numerical simulation enables the evaluation and the study of the electric field intensity distribution pattern around the plasmonic nanostructures.

Figure 1:
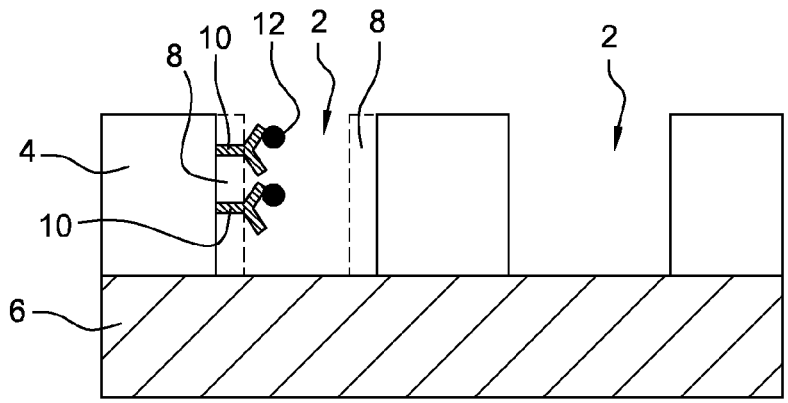
FIG. 1: is a principle drawing of a conventional SPR sensor with nanohole array.

In the conventional design of L-SPR based sensors with nanohole arrays, as .e.g. shown in FIG. 1, cylindrical holes/cavities 2 are drilled (e.g. by ion beam) in the plasmon resonance supporting metal layer 4 laying over the dielectric substrate 6. In this case the electric field pattern in the cavity 2 is maximum along the cylindrical walls as represented by the vertical dark grey rectangles 8 in FIG. 1. The typical distance from the wall of the strongest electric field is of around 10 nm.

In biosensor applications, receptor moieties, e.g. proteins, are typically immobilized in the cavities, these moieties having a binding specificity for analytes to be detected in the sample. Typically, the receptor moieties are hence fixed onto the walls of the cavities where the electric field is maximum.

However, receptor moieties have finite dimensions; antibodies for example have a typically length ranging from 10 to 20 nm.

It will thus be understood that with an electric field of about 10 nm, it is actually the receptor moiety which is located in the region where the electric field of the plasmonic resonance is maximum.

When the analyte reaches the cavity, it is recognized by the bioprobe and it is immobilized on the bioprobe receptor itself creating a complex.

But the analyte will be situated in a region of the cavity 2, which is relatively outside the maximum intensity of the electric field and so it will not be sensed with the optimum sensitivity.

This situation is illustrated in FIG. 1, where antibodies indicated 10, forming receptor moieties, are fixed on the lateral walls of the cavity 2. The extension of the antibodies 10 may be compared with the width of region of strong electrical field 8. Reference sign 12 indicates an antigen bound to a receptor antibody 10. This analyte 12 present in the test sample has unique binding specificity to the antibody 10 and thus combines therewith to form a complex. However, due to the reduced extension of the strong electric field, this binding occurs outside thereof.

b) Operating Principle of the Present Sensor

Figure 2:
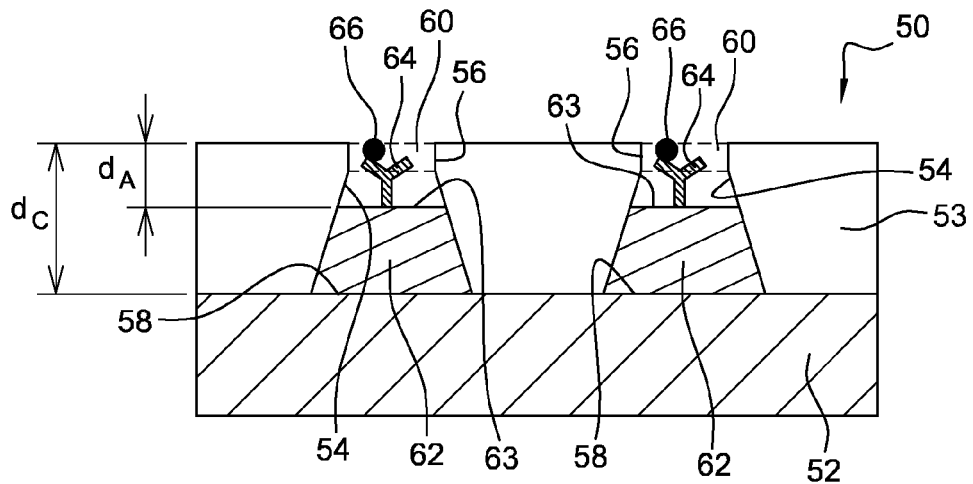
FIG. 2: is a sketch illustrating the design principle of the present SPR sensor device.

The present concept of sensor design is illustrated in FIG. 2. In order to optimize the sensitivity of the L-SPR sensor, the present inventors have configured the geometry of the cavities in order to obtain a strong/enhanced electrical field pattern in one region of the cavity, and have found a means for arranging the receptor moieties contiguously to, or with a partial overlap with, this region of strong electrical field so that analytes binding to the receptor moieties are located in this strong electrical field, hence in a region of maximum/enhanced sensitivity.

Referring to FIG. 2, the present SPR sensor device 50 comprises a dielectric substrate 52 with an L-SPR supporting layer comprising a noble metal layer 53 on the dielectric substrate 52 with an array of nano-cavities 54 therein (only a couple of cavities 54 being shown here for simplicity). The dimensions of the cavities 54 are typically called "sub-wavelength", i.e. they are inferior to the wavelength of the probe light beam. The cavities 54 are designed to be asymmetric, i.e. their cross-section is not constant over the whole cavity depth so as to be asymmetric over the direction of the incoming light beam. But more specifically, the cavities 14 have a shape that widens from their aperture 56 to their bottom 58, the closed bottom of the cavity being formed by the surface of the underlying substrate 52. The broadening can be continuous as in FIG. 2, e.g. based on a truncated cone or pyramidal shape, or designed as a stepped profile. The depth of the cavity 54, noted $d_C$ represents the vertical distance from opening 56 to bottom 58. When such a SPR-sensor is illuminated with the probe light from the substrate side, i.e. from its widest, bottom side 58, at appropriate angle and wavelength, plasmon resonance is excited. The field strength of surface plasmon polaritons is strong, reaching maximum levels, about the opening section 56 of the cavity, as illustrated by the rectangle 60 in FIG. 2.

The ability to tailor the magnetic response of nanohole arrays is well known in the art (see e.g. the article by Li, J. et al. "Studies of the plasmonic properties of two-dimensional metallic nanobottle arrays" in APPLIED PHYSICS LETTERS 92, 213106 (2008)). Indeed, the excitation and radiation of surface plasmon polaritons are highly geometry dependent; the resonance is dependent on the size and shape of the metal nanostructure. It has also been shown that the spectral position of surface plasmon polaritons is mainly dependent on the period of the array of nanocavities, whereas the field strength and pattern are strongly dependent on the actual shape of the cavity arranged in the metal layer.

As mentioned, the asymmetric shape of the cavity 54 (broadening from open to bottom) leads to a concentration of the strongest electric field about the cavity's opening 56. The geometry/dimensions of the cavity 54 are hence chosen to obtain a desired electromagnetic response It shall be appreciated that the present sensor device 50 further includes a bed 62 of dielectric material lying on the bottom 58 of the cavity 54 that reduces the apparent depth of the cavity 54. Hence, while the hole in the metal layer 53 still has a depth $d_C$ (corresponding to the thickness of the metal layer—the cavity is a through hole), the bottom of the cavity is filled with dielectric material and thus appears to have a depth $d_A$, representing the distance from the opening 56 top to the surface of the bed 62. This bed 62 forms a kind of support structure or pedestal, on the surface 63 of which receptor moieties 64 can be attached in the close vicinity of the region of strong electric field. Hence, when the corresponding analyte will bind to a receptor moiety, it will be located in the region of maximum sensitivity. In other words, the cavity 54 is partly filled with the dielectric material constituting the bed 62, so that it is open from the top of metal layer and hollow over the depth corresponding to the apparent depth $d_A$.

This is illustrated in FIG. 2 where the receptor antibody 64 is attached to the surface 63 of bed 62 and has its opposite extremity interfacing with the region of strong electric field pattern 60. Upon binding with the antibody 64, the cogent antigen 66 will then extend in this maximum electric field region 60, hence in the region of maximum sensitivity.

Figure 3:
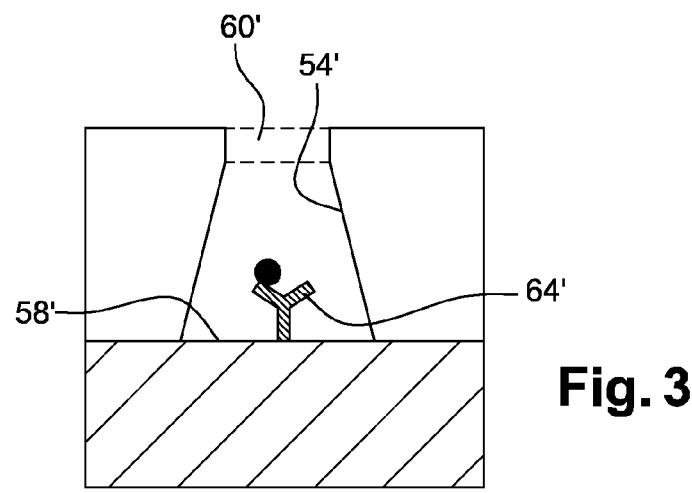
FIG. 3: is a comparative sketch (not an embodiment of the present SPR sensor), illustrating the location of the receptor moiety at the bottom of the cavity without dielectric bed.

For comparative purposes, FIG. 3 illustrates a SPR sensor structure being designed with a similar conical cavity 54' as the sensor of FIG. 2, however lacking the dielectric bed. As can be seen, the antibody 64' would be located at the very bottom 58' of the cavity and even upon binding, the formed complex would be quite far from the region of strongest electric field 60'. It has to be kept in mind that in such nanostructures the hole depth $d_C$ is typically of no less than 100 nm, while the typical size of an antibody is 15 nm.

Turning back to the present sensor as shown in FIG. 2, attachment of the receptor moieties is conveniently achieved through a functionalized surface of the material forming the bed 62. The functionalization of the material is done to have a selective binding to a desired type of receptor moieties, the latter being select depending on the type of test to be carried out. A suitable material for the functionalized polymer is polyacrilic-acid or any dielectric polymer with suitable functionalities for optimized attachment of the target moieties.

Although in FIGS. 2 and 3 the bed 62 is shown as a single layer, it may comprise two or more layers of dielectric material. For example a first layer of dielectric material may lie over the cavity bottom, and a second layer of dielectric is formed over the first layer. In such case, the top surface of the second (or topmost) layer forms the surface of the bed, and the thickness of the bed is the sum of the individual thicknesses of each layer. The dielectric material of the second (or top) layer has the desired functionalization to attach the probes (receptor moieties); porous dielectrics including hydrogels may be used for the second/top layer.

Figure 4:
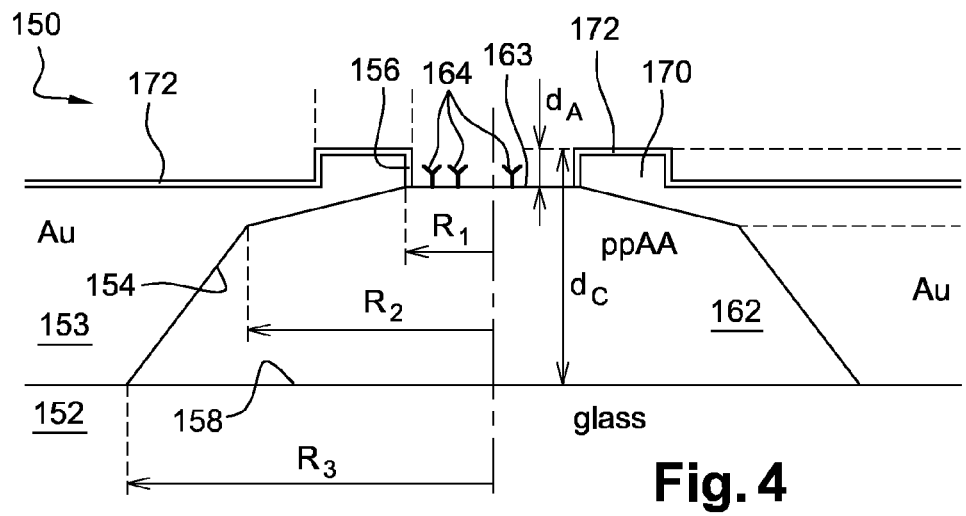
FIG. 4: is a layout view of the nanostructure according to an embodiment of the present SPR sensor.

A practical embodiment of the present sensor device is illustrated in FIG. 4. Similar features are indicated by same reference signs as in FIG. 2, increased by 100. The sensor device 150 is constructed in accordance with the above-explained design principle. The sensor device 150 comprises a dielectric substrate 152 made from glass. A layer of noble metal, here gold, is indicated 153 and lays over the glass substrate 152. This layer comprises an array of cavities 154 formed in the gold layer, although only one is shown here for simplicity. The cavity 154 in the metal has a depth noted $d_C$. It has a step-wise widening cross-section that comprises three sections: an opening section with a radius R1, an intermediate section with a maximum radius R2 and a terminal section with a maximum radius R3. It may be noted that the aperture 156 of the cavity is configured as a collar section 170 slightly protruding over the surface of the metal layer 153.

The cavity 154 is partially filled with dielectric material forming a bed 162 that reduces the apparent depth of the cavity to a depth $d_A$. The surface of the bed 162 is functionalized to allow attachment of receptor moities thereon, as illustrated by the antibodies 164 represented in FIG. 4.

For the sake of exemplification, we shall comment on the materials and dimensions, but these shall not be construed as limitative. Instead of a glass substrate 152, one may use other transparent dielectric materials, e.g. transparent polystyrene or PMMA or polycarbonate; alternatively, semiconductor material may be used, preferably with low doping). Also instead of gold, other metals may be used, e.g. noble metals such as Ag and Pt, or Al. The dielectric material of the bed 162 may be ppAA, or any other appropriate functionalized polymer. The gold layer has a thickness in the order of 120 nm about the cavity opening; the cavity depth $d_C$ is thus 120 nm. The thickness of the bed 162 is 100 nm, whereby the apparent depth $d_A$ is 20 nm. The radius at the opening is R1=50 nm while at the bottom of the cavity R3=200 nm. Again, these dimensions are given for the sake of exemplification and are not to be construed as limiting in any manner.

Figure 5:
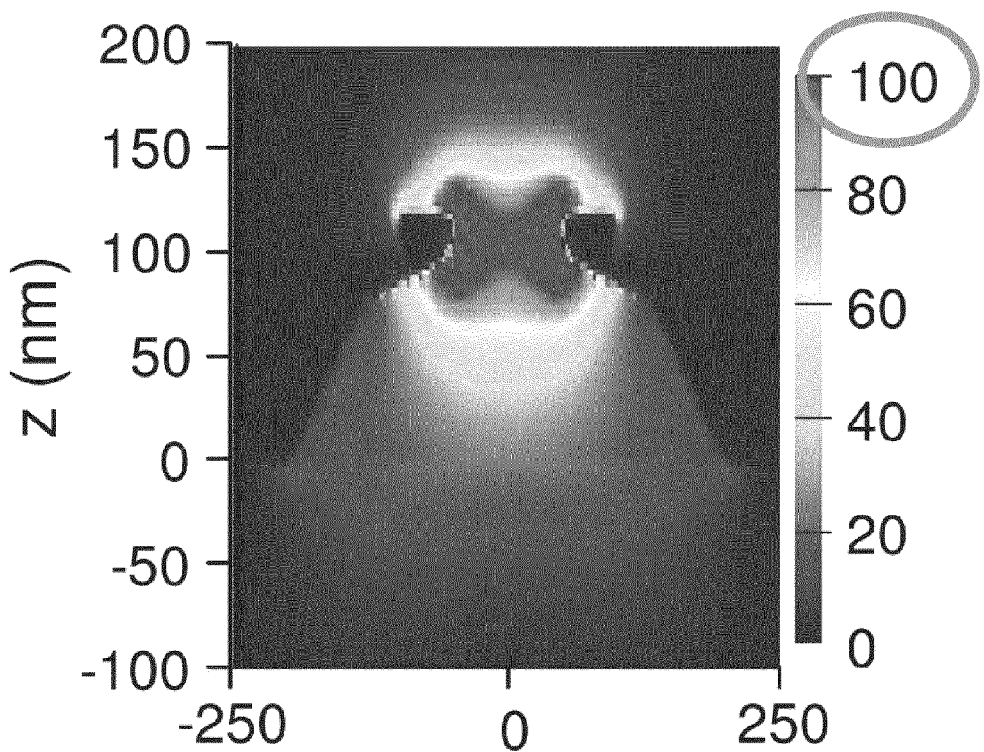
FIG. 5: is a view illustrating the electric field intensity pattern inside and around the nanostructure.

The electrical field pattern under plasmonic resonance for the nanostructure of FIG. 4 has been determined by numerical simulation and the electrical field distribution is represented in FIG. 5. As can be seen, bearing in mind the above assumptions of shapes and dimensions, a region of strong electrical field exists about the opening section 156 of the cavity; due to the height of the bed, and hence to the position of the receptor moieties, any analyte binding to a receptor moiety will be located in the region of maximum sensitivity.

Preferably, a thin layer of antifouling material 172 is formed over the metal surface (thus not on the bed surface 163). As it is known, the antifouling material acts in an antiadhesive manner to prevent or reduce undesired interactions, such as the non-specific absorption of chemical or biochemical molecules etc. . . . This reduces noise signals that could have been caused by the interaction or the binding of undesired chemical or biochemical molecules at the sensor surface.

c) Manufacture of the Sensor

The present sensor can be easily manufactured using lithographic techniques. A possible manufacturing technique is the following. A layer of poly acrylacid (ppAA) is deposited over a glass substrate; and a subsequent layer of polystyrene beads (PS) are deposited over the ppAA. The ppAA and PS layers are etched by O2 plasma to form a grating structure comprising regularly spaced pillars of ppAA separated by a sub-micrometric distance. The pillars have a tapering shape from their basis to top. Gold is then deposited over the pillars to fill-in the gaps between neighbouring pillars, and the remainder of the PS mask is removed, obtaining a periodic gold nanograting. Other possible materials for the dielectric pillars are polystyrene or poly-methyl-methacrylate, etc.

It may be noted that at this stage the cavities are completely filled with the dielectric material of the pillars. To form the cavities with a bed for attaching and locating the receptor moieties, it then suffices to selectively (with respect to gold) etch the top of the pillars down to the desired apparent depth dA. An advantage of this technique is that the ppAA etching can be conducted with a great precision, i.e. of about ±2 nm.

The thin layer of antifouling material (e.g. antifouling hydrogel, namely poly-ethylene glycol) may then be selectively deposited on the exposed gold surfaces.

d) Use in a SPR Sensing System

Figure 6:
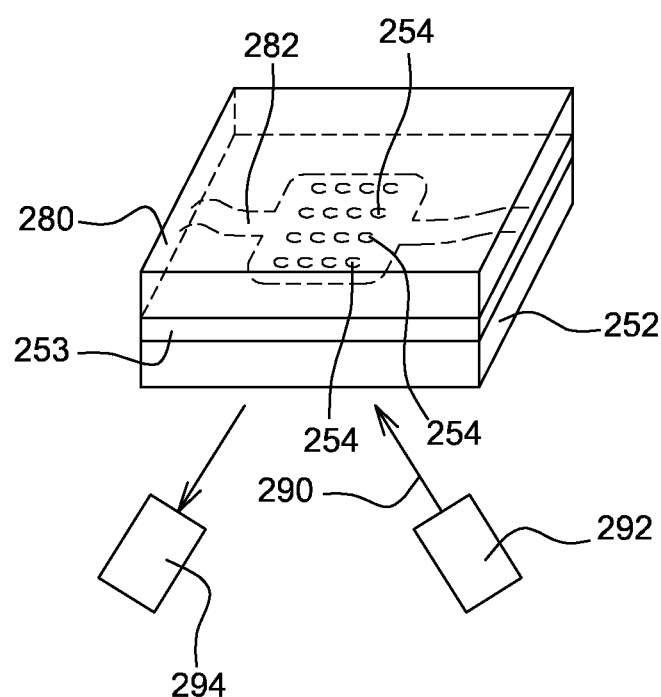
FIG. 6: is a principle diagram of an embodiment of SPR sensing system.

Turning now to FIG. 6, there is schematically represented a SPR sensing system comprising a SPR sensor device as described above. In operation, the sensor is orientated so that the probe light is incident from the substrate 252 side and thus illuminates the cavities 254 from the widest, bottom size, i.e. opposite from the opening. Typically, the sensor device comprises at least one array of cavities 254 designed according to the present principle to support L-SPR and achieve the above-described electrical field pattern.

In such practical embodiment, the metal layer 253 is covered by a micro-fluidic system 280 comprising channels that permit to selectively bring a test sample in contact with a respective array of cavities 254. In such case, each array may be prepared to contain different receptor moieties to detect different substances. The microfluidic system 280 may be carried out by forming on top of the metal layer 253 an elastomer layer or other materials (e.g. PDMS, PMMA, Glass, Epoxy, etc.) with channels 282 formed therein, as is known in the art.

In use, the present SPR sensor device is thus illuminated from the substrate side by a test light beam 290 (probe beam) originating from an input optical module 292. Test light beam 290 having a frequency and incident angle known to be able to excite SPR at the sensor surface. It may be noted that the test light beam 290 illuminating the nanocavities array may be configured in a manner known per se to have a given polarization. In order to excite SPR, the test light beam 290 has one or more frequencies that match with one or more permitted frequencies of the surface-bond electromagnetic waves at the sensor nanostructure. Preferably, the sensor is designed so that the permitted frequencies of SPR correspond typically to the visible/near-infrared spectrum of light. As the test light beam excites SPR, at least part of the test light beam is absorbed at the sensor surface, where the extent of absorption depends on the frequency of the incident light at the sensor surface. The light of the test light beam that has not been absorbed at the sensor surface is then reflected and intercepted at an output optical module 294. One may note that operation in transmission mode is also possible.

Then a light property of the reflected test light beam, preferably its intensity, is sensed (measured) in the output optical module 294 and an actual value of the measured light property is determined, which is representative of the level of excitation of the surface plasmons and allows assessing a state of resonance or the shift of the resonance condition established with respect to calibrated or previously stored/acquired data. As it is known, a resonance condition typically leads to a decrease in the measured intensity of the reflected light of the test light beam due to the absorption of the light at the sensor surface, and a modification in the refractive index of the sample adjacent to the sensor surface causes a shift of the resonance condition.

As it will be understood by those skilled in the art, the detection/measure in the output optical module may be carried out by means of a photodetector or imaging array.

d) Use in a Other Sensing Techniques

As explained above, the present sensor device can be advantageously used in other detection techniques. Indeed, the L-SPR effect (oscillation of the electrons of the noble metal layer localized just around the nanocavity) produces, in combination with the tapering shape of the nanocavities, an enhanced electric field around the cavity opening, which may be beneficial to other analysis techniques, such as Raman/SERS, Fluoescence spectroscopy and SALDI.

As a matter of fact, the electric field plays a role in all of these applications and one may note that:

in Raman Spectroscopy (SERS), the electric field determines the strength of the Raman emission, hence the Raman signal and sensitivity.

in Fluorescence Spectroscopy, the electric field (at a special wavelength) is the one exciting the fluorescent molecules to emit their light. Hence, locating the fluorescent molecule on the top of the cavity, where the electric field is maximum, will act as in increase of the emitted light and so of the sensitivity.

in SALDI the proteins to be analyzed by Mass Spectrometry are induced to be desorbed using a high energy laser, which locally increases the temperature. The energy of the laser beam (hence the thermal power it can release to the surface) is proportional to the strength of the electric field. By using the present sensor, it is possible to concentrate the electric field where the molecules are located, and thereby optimize the desorption.

The invention claimed is:

1. A sensor device comprising:
a dielectric substrate;
a metal layer on said substrate with at least one array of nano-cavities therein and adapted to support L-SPR, each of said cavities of the at least one array of nano-cavities in said metal layer having a depth, an opening and a closed bottom and widening from opening to bottom in order to form a strong electrical field pattern around the cavity opening;
wherein a bed of dielectric material having a thickness that is less than the depth of said cavities is provided over the bottom of each cavity of the at least one array of nano-cavities to form a reduced, apparent depth, the bed surface being functionalized to bind to receptor moieties;
wherein the thickness of said dielectric bed is designed such that upon binding of an analyte to said receptor moieties, said analyte is at least partially located in the region of strong electric field.

2. The sensor device according to claim 1, wherein said cavities of the at least one array of nano-cavities have a frusto-conical or trapezoidal shape from opening to bottom.

3. The sensor device according to claim 1, wherein the widening of said cavities of the at least one array of nano-cavities is continuous or in a stepped manner.

4. The sensor device according to claim 1, wherein the cavities of the at least one array of nano-cavities are closed at their bottom by the dielectric substrate.

5. The sensor device according to claim 1, wherein the thickness of said bed is inferior to the depth of the cavity.

6. The sensor device according to claim 1, wherein the height of said bed is such that said apparent depth is in the range of 10 to 30 nm from the opening.

7. The sensor device according to claim 1, wherein the height of said bed is such that said apparent depth is in the range of 15 to 25 nm.

8. The sensor device according to claim 1, wherein said bed consists of functionalized dielectric polymer, at least in surface.

9. The sensor device according to claim 1, wherein said bed is made from a single dielectric polymer; or from two or more layers of dielectric material, the top layer comprising a functionalized dielectric polymer.

10. The sensor device according to claim 1, wherein said metal layer has a thickness of at least 100 nm.

11. The sensor device according to claim 1, wherein said metal layer is made from a metal comprising gold, silver, copper, platinum, or aluminium, or an alloy comprising one or more thereof.

12. The sensor device according to claim 1, wherein said cavities of the at least one array of nano-cavities have an opening width in the range of 50 to 250 nm, a bottom width in the range of 100 to 450 nm, and a cavity depth in the range of 100 to 200 nm.

13. The sensor device according to claim 1, wherein said at least one array of cavities has a periodicity of in the range of 200 to 1000 nm.

14. The sensor device according to claim 1, wherein said at least one array of cavities has a periodicity of in the range of 200 to 1000 nm.

15. The sensor device according to claim 1, wherein the metal layer is covered with a layer of anti-fouling material.

16. The sensor device according to claim 1, comprising receptor moieties attached to the bed surface.

17. The sensor device according to claim 1, wherein the at least one array of nano-cavities comprises a plurality of arrays of nano-cavities, each array comprising a respective receptor moiety, and further comprising a microfluidic layer on top of said metal layer, said microfluidic layer comprising channels arranged to selectively bring a test sample in contact with a selected array of nano-cavities and the respective receptor moiety.

18. The sensor device according to claim 1, wherein said substrate comprises dielectric material and/or semiconductor material.

19. A sensor device according to claim 1 configured for use in a detection method based on one or more of: SPR, SERS, fluorescence and SALDI.

20. A SPR sensing system comprising:
a sensor device according to claim 1;
an input optical module emitting at least one test light beam for illuminating the L-SPR supporting metal layer of said sensor device under conditions selected so as to excite SPR;
an output optical module to measure a light property of said at least one test light beam as transmitted or as reflected by the sensor device so as to monitor a condition of resonance at the sensor surface.

21. A SPR sensing system comprising according to claim 20, wherein said sensor device is illuminated with said at least one test light beam from the dielectric substrate side.

22. A sensing system comprising a sensor device according to claim 1, wherein said sensing system is configured to operate chemical, molecular, biochemical or bio-molecular detection based on SPR, SERS, fluorescence and/or SALDI.

* * * * *